(12) United States Patent
Brajnovic et al.

(10) Patent No.: US 8,038,445 B2
(45) Date of Patent: Oct. 18, 2011

(54) METHODS OF FORMING AT LEAST ONE HOLE IN A JAW BONE

(75) Inventors: Izidor Brajnovic, Goteborg (SE); Thomas Eriksson, Goteborg (SE)

(73) Assignee: Nobel Biocare Services, AG, Zurich-Flughafen (CH)

( * ) Notice: Subject to any disclaimer, the term of this patent is extended or adjusted under 35 U.S.C. 154(b) by 97 days.

(21) Appl. No.: 12/465,482

(22) Filed: May 13, 2009

(65) Prior Publication Data

US 2009/0239200 A1    Sep. 24, 2009

Related U.S. Application Data

(60) Division of application No. 11/172,292, filed on Jun. 30, 2005, now Pat. No. 7,665,989, which is a continuation of application No. PCT/SE03/01977, filed on Dec. 19, 2003.

(30) Foreign Application Priority Data

Dec. 30, 2002 (SE) ........................................ 0203900

(51) Int. Cl.
*A61C 5/00* (2006.01)
(52) U.S. Cl. ........................................ 433/215; 433/165
(58) Field of Classification Search .................... 433/82, 433/144, 165–166, 197–198, 24, 215, 224
See application file for complete search history.

(56) References Cited

U.S. PATENT DOCUMENTS

| 362,934 | A | * | 5/1887 | Champion | ..................... 408/224 |
| 1,333,388 | A | * | 3/1920 | Chester | ......................... 433/165 |
| 1,643,679 | A | | 9/1927 | Roderick | |
| 2,392,519 | A | | 1/1946 | Beavon | |
| 2,543,206 | A | | 2/1951 | Smith | |

(Continued)

FOREIGN PATENT DOCUMENTS

EP    0412845 A1    2/1991

(Continued)

OTHER PUBLICATIONS

International Search Report in Application No. PCT/SE2003/001977 (the PCT counterpart of the parent application).

*Primary Examiner* — Cris L Rodriguez
*Assistant Examiner* — Hao D Mai
(74) *Attorney, Agent, or Firm* — Knobbe Martens Olson & Bear, LLP

(57) ABSTRACT

A method is provided for forming a hole in a jaw bone at a drill site. The method can comprise forming an initial hole in soft tissue of the jaw bone, advancing a first portion of the drill through the soft tissue and into a bone portion of the jaw bone to form a guidance hole in the bone portion of the jaw bone, advancing the drill until a second portion of the drill contacts the soft tissue to form an enlarged hole in the soft tissue, and further advancing the drill until the second portion of the drill contacts the bone portion of the jaw bone to form a countersink hole in the bone portion. The countersink hole can be formed to have a flat bottom that is immediately adjacent to an inclined surface thereof.

26 Claims, 2 Drawing Sheets

U.S. PATENT DOCUMENTS

| | | | |
|---|---|---|---|
| 2,715,772 A * | 8/1955 | Fritz | 433/165 |
| 2,782,824 A | 2/1957 | Robinson | |
| 2,898,787 A | 8/1959 | Hofbauer | |
| 3,346,894 A | 10/1967 | Lemelson | |
| 3,564,948 A | 2/1971 | Pomernacki | |
| 3,920,350 A | 11/1975 | Southall | |
| 4,341,206 A | 7/1982 | Perrett et al. | |
| 4,345,899 A | 8/1982 | Vlock | |
| 4,480,952 A | 11/1984 | Jeremias | |
| 4,738,616 A * | 4/1988 | Reynaud | 433/220 |
| 4,854,871 A * | 8/1989 | Weissman | 433/166 |
| 4,978,350 A | 12/1990 | Wagenknecht | |
| 4,990,088 A * | 2/1991 | Weissman | 433/165 |
| 5,007,911 A | 4/1991 | Baker | |
| 5,051,092 A * | 9/1991 | Miller | 433/225 |
| 5,066,230 A * | 11/1991 | Weissman | 433/165 |
| 5,098,293 A * | 3/1992 | Loof et al. | 433/165 |
| 5,184,689 A | 2/1993 | Sheirer et al. | |
| 5,193,951 A | 3/1993 | Schimke | |
| 5,221,166 A | 6/1993 | Bothum | |
| 5,259,398 A * | 11/1993 | Vrespa | 128/898 |
| 5,259,707 A | 11/1993 | Keller | |
| 5,366,468 A | 11/1994 | Fucci et al. | |
| 5,569,035 A | 10/1996 | Balfour et al. | |
| 5,573,537 A | 11/1996 | Rogozinski | |
| 5,593,410 A | 1/1997 | Vrespa | |
| 5,636,989 A * | 6/1997 | Somborac et al. | 433/173 |
| 5,697,738 A | 12/1997 | Stone et al. | |
| 5,741,267 A * | 4/1998 | Jorneus et al. | 606/102 |
| 5,782,636 A * | 7/1998 | Armstrong et al. | 433/165 |
| 5,788,497 A * | 8/1998 | Chalifoux | 433/220 |
| 5,839,897 A * | 11/1998 | Bordes | 433/165 |
| 5,871,356 A | 2/1999 | Guedj | |
| 5,997,298 A * | 12/1999 | Nowak | 433/165 |
| 6,059,789 A | 5/2000 | Dinger et al. | |
| 6,068,632 A | 5/2000 | Carchidi et al. | |
| 6,146,138 A * | 11/2000 | Dalmau | 433/141 |
| 6,179,615 B1 * | 1/2001 | Blacklock et al. | 433/165 |
| 6,227,774 B1 | 5/2001 | Haughton et al. | |
| 6,312,432 B1 | 11/2001 | Leppelmeier | |
| D455,446 S | 4/2002 | Collins | |
| 6,902,400 B1 | 6/2005 | Roetzer | |
| 6,916,322 B2 * | 7/2005 | Jesch | 606/80 |
| 7,140,814 B2 | 11/2006 | Singh et al. | |
| 7,210,933 B2 * | 5/2007 | Haessler | 433/174 |
| 7,547,210 B1 * | 6/2009 | Valen | 433/165 |
| 2002/0031745 A1 | 3/2002 | Kumar et al. | |
| 2003/0022132 A1 | 1/2003 | Jesch | |
| 2004/0063067 A1 * | 4/2004 | Takahashi et al. | 433/165 |
| 2004/0081940 A1 | 4/2004 | Roetzer et al. | |
| 2004/0152045 A1 | 8/2004 | Kachalon | |
| 2005/0003327 A1 | 1/2005 | Elian et al. | |
| 2006/0121415 A1 | 6/2006 | Anitua Aldecoa | |
| 2006/0210949 A1 * | 9/2006 | Stoop | 433/165 |
| 2008/0085488 A1 * | 4/2008 | Lazarof | 433/50 |
| 2009/0024129 A1 | 1/2009 | Gordon et al. | |
| 2009/0116918 A1 | 5/2009 | Dost et al. | |
| 2009/0305189 A1 * | 12/2009 | Scortecci et al. | 433/165 |

FOREIGN PATENT DOCUMENTS

| | | |
|---|---|---|
| EP | 424 734 A1 | 5/1991 |
| EP | 424734 | 5/1991 |
| FR | 1038475 | 9/1953 |
| JP | 6304187 | 11/1994 |
| WO | WO 96/20803 | 7/1996 |

* cited by examiner

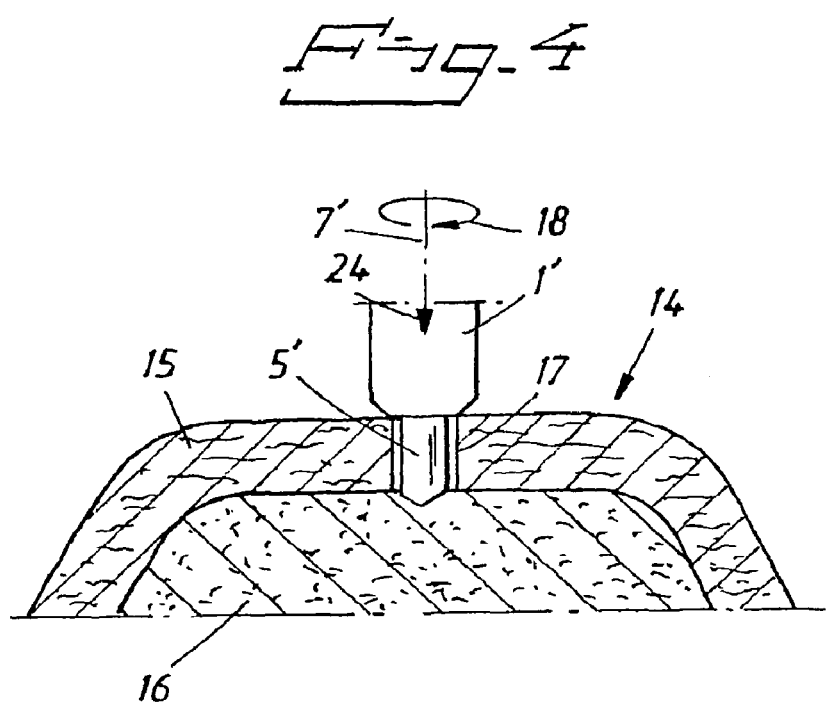
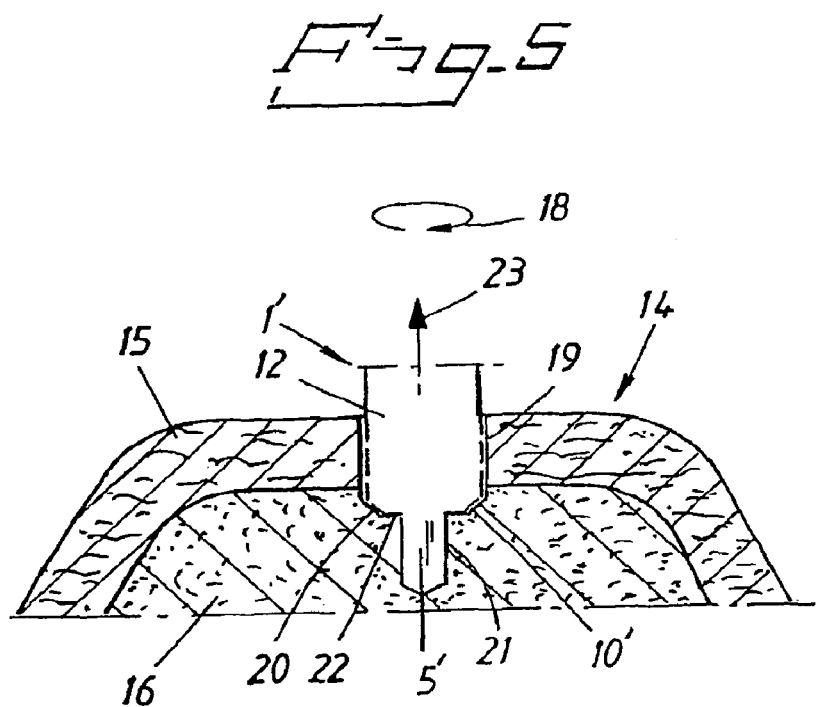

METHODS OF FORMING AT LEAST ONE HOLE IN A JAW BONE

PRIORITY INFORMATION

This application is a divisional of U.S. patent application Ser. No. 11/172,292, filed on Jun. 30, 2005, which is a continuation of International Application PCT/SE2003/001977,, with an international filing date of Dec. 19, 2003, which claims priority under 35, U.S.C. §119, to Swedish Patent Application No. SE 0203900-6, filed Dec. 30, 2002; the entire contents of each application are expressly incorporated by reference herein.

BACKGROUND OF THE INVENTION

1. Field of the Invention

The invention also relates to a drill for use in dentistry and having said structure, and more particularly, to a drill which can be used on a jaw bone with overlying soft tissue and underlying, more solid bone.

2. Description of the Related Art

The drill is intended to be used in conjunction with the arrangement sold by Nobel Biocare AB Sweden under the name ARK (Absolute Rehabilitation Kit). Reference is made in purely general terms to the PCT applications WO 02/053055, A1, WO 02/053056, A1, and 02/053057, A1, filed by the same Applicant as for the present patent application. Reference is also made to what is generally already known in the technical field of drills.

Holes are formed in the jaw bones of patients in various circumstances and implantation situations. In cases where it is necessary to form a hole in the jaw bone, it is already known to mark out the drilling site initially and thereafter to expose the underlying jaw bone surgically and drill the hole using one or more first drills. Thereafter, a special countersinking drill is used to form a countersink intended for the head or outer part of an implant. Said drilling function has hitherto been performed using at least three different drills.

There is a need to be able to simplify and improve the hole formation function so that cutting-open of the soft tissue can be avoided and fewer drilling stages are needed, and so that the result of the hole formation is still satisfactory or can plainly be improved. It is a considerable advantage if the process of exposing the bone can be eliminated and the number of instruments and drills can be reduced without compromising the precision of the hole formation. It is also expedient if the same or similar instruments as used previously can also be used in the new context.

SUMMARY OF THE INVENTION

It is an object of the present invention is to solve at least some of the aforementioned problems. Accordingly, one aspect of the present invention comprises a drill that has a first portion designed to cooperate with the soft tissue to form an initial hole in the latter and a second portion that is designed to cooperate with the soft tissue and the more solid underlying bone for enlargement of said hole and for formation of a countersunk hole in the more solid bone. A further characteristic is that the first portion is also designed to cooperate with the more solid bone, during the second portion's formation of the countersunk hole, in order to produce a guidance hole and/or marker hole in the bottom of the countersink.

In other embodiments of the present invention, the number of first and second cutting edges can be two, three or four. The first portion can be plate-shaped and arranged in the longitudinal direction of the drill. The plate-shaped first portion can have a length of about 1.5, mm and is also designed with a tip through which the center line of the drill extends. The first portion has the first cutting edges arranged along its sides. The second cutting edges are inclined in order to form an inclined surface in the countersink. The inclination of the surface is arranged so that the surface narrows inward in a cone shape as seen in the hole formation direction. The second cutting edges can also be arranged with rectilinear parts for removing the material (gum) that arises during drilling. Further characteristics of the drill are set out in the attached dependent claims referring back to independent claim 1.

Another embodiment of the present invention comprises a drill for use in dentistry with a first portion that is arranged at the front or distal end of the drill in order to form an initial hole, and in that a second portion that is designed to enlarge said hole and form a countersunk hole. The first portion is also designed in such a way that, during the second portion's formation of the countersunk hole, it produces a guidance hole and/or marker hole in the bottom of the countersink.

Another embodiment of the present invention includes a drill that comprises a first portion which is provided with one or more first cutting edges and with a first width or diameter, and, arranged behind the first portion, a second portion which is provided with one or more second cutting edges and with a second diameter exceeding the first width or diameter.

By what has been proposed above, the problems mentioned in the introduction are solved. With the new drill, the hole formation sequence can be changed around so that, for example, in contrast to previously known techniques, the countersunk hole is formed before the hole is drilled. In connection with the formation of the countersunk hole, the bottom of the countersink is marked out, which considerably facilitates application of the drill used for the continued hole formation in the jaw bone. This has the advantage of eliminating the need for separate marking and countersinking drills, these having now been combined in one unit.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A presently proposed embodiment of a drill according to the invention will be described below with reference to the attached drawing, in which:

FIG. 4 is a diagrammatic longitudinal section showing a first stage of using the drill on a jaw bone which comprises a soft tissue part or gum and, located under this, more solid bone, for example cortical bone.

FIG. 5 shows, again in a diagrammatic longitudinal section, the use of the drill in a second stage.

DETAILED DESCRIPTION OF THE PREFERRED EMBODIMENT

Figure 1:
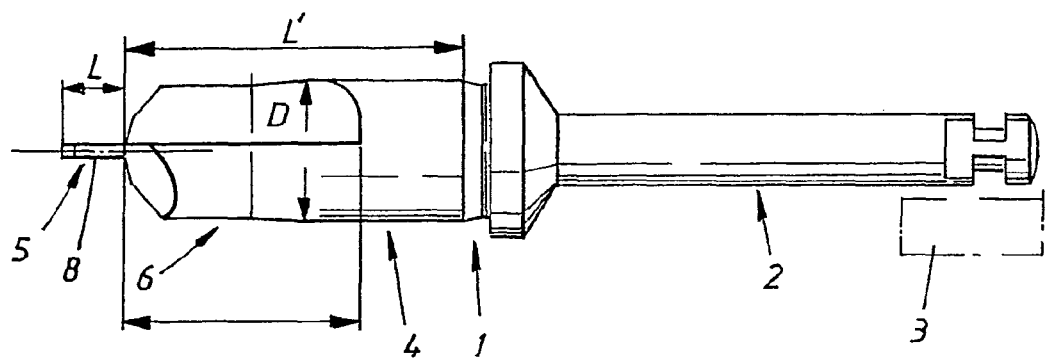
FIG. 1 shows the drill in a longitudinal view.
Figure 2:
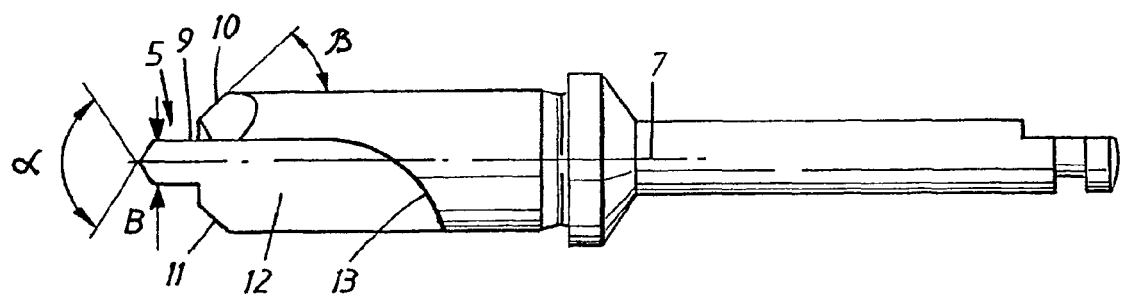
FIG. 2 shows the drill according to FIG. 1 in a longitudinal view, but turned 90°, about its longitudinal axis.

In FIG. 1, the drill as a whole is designated by 1. The drill comprises an attachment by which the drill is connected to a drilling machine indicated only symbolically by reference number 3. The drill also has a part 4 which bears the cutting edges in question. The part 4 comprises a first or front portion 5 and a second portion 6. In the illustrative embodiment, the front portion 5 has the shape of a plate, and in FIG. 1 the plate-shaped portion 5 is shown from the side, while FIG. 2 shows the first portion 5 in a view in which it has been turned 90°, in relation to FIG. 5. The view according to FIG. 2 shows that the plate-shaped portion 5 has a tip whose angle has been indicated by α. In the illustrative embodiment, the angle is chosen at about 120°. The tip is arranged so that the center line 7 of the drill extends through the tip. The plate-shaped portion 2 is further equipped with two first cutting edges, the first cutting edge having been designated by 8 and the second cutting edge having been designated by 9. The first cutting edges 8, 9 are thus arranged on both sides of the square-shaped part of the plate-shaped portion. The portion 5 can be given an alternative design, for example the number of first cutting edges 8, 9 can be increased with further cutting edges, so that the total number of first cutting edges can be three, four, etc. It is also possible per se to use only one cutting edge although such an embodiment is not as advantageous. At its front parts, the second portion 4 is provided with cutting edges 10, 11 which are inclined in relation to the center axis 7. Said second cutting edges are situated to the side of the center line 7 and extend with angles β in relation to the center line which can be chosen at 45°. The second portion is also provided with recesses 12 via which material which arises during drilling in the jaw bone can be removed rearward and out to the side of the drill. The recesses are thus shaped with a rear curved wall 13. The number of second cutting edges can be varied and can, for example, be chosen as two, three, four, etc., cutting edges. The configuration with first and second cutting edges and first and second portions can also be seen from the end view according to FIG. 3 where, inter alia, the portion 5, the cutting edge 8, the cutting edges 10 and 11, and the space 12 have been indicated. The first portion 5 is thus arranged at the front end of the drill, and the second portion 4 is arranged behind the first portion. The first portion can have a length L of about 1.5 mm. The second portion can have a length L' of about 11 mm. The plate-shaped member can be arranged with a maximum width B, see view according to FIG. 2, of the order of 1.5 mm. The second portion can be designed with a diameter of about 4.7 mm. The plate-shaped portion can have a thickness of about 0.4 mm.

Figure 3:
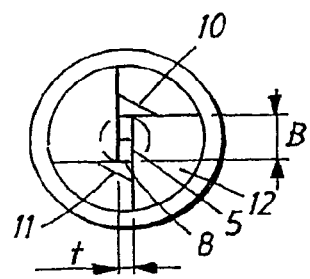
FIG. 3 is an end view of the drill according to FIG. 2, from the front.

FIGS. 4 and 5 show hole formation in a jaw bone 14 in two stages using the drill according to FIGS. 1, 2 and 3. The jaw bone comprises a soft tissue part or gum 15 and, located under the soft tissue, a harder and more solid bone 16, which can be cortical bone and/or trabecular bone. FIG. 4 shows the first stage in which the partially shown drill 1' is arranged with the first portion 5' penetrating through the soft tissue 5. During this penetration into and drilling of the soft tissue 15, a hole 17 is formed which, in FIG. 4, is shown slightly enlarged, for the sake of clarity, in relation to the first portion 5'. In the figure, the rotation about the center axis 7' of the drill is indicated by reference number 18. The soft tissue 15 can be drilled without having to cut open the soft tissue part at the drill site, as was previously necessary. In the case shown in FIG. 5, the drill has penetrated deeper into the gum 14. The hole 17 according to FIG. 4 has been enlarged and the enlarged hole in the soft tissue 15 has been indicated by 19. In this case too, the hole 19 has been shown enlarged in relation to the drill 1' for the sake of clarity. In addition to the enlargement of the hole 17 to give the hole 19, the drill in the stage shown in FIG. 5 has been moved down into the harder or more solid part of the jaw bone. This downward movement has meant that a countersunk hole 20 has been obtained in the more solid or harder bone 16. The countersink is produced using the inclined second cutting edges 10, 11 (cf. FIG. 2) on the second portion. The surface 20 in the countersink has the shape of a truncated cone and the cone angle of the surface corresponds to the one obtained with the inclined surfaces 10, 11. An inclined surface has been indicated by 10' in FIG. 5. In addition to the function of forming the countersink 20, the drill has additionally produced a guidance hole and/or marker hole 21 at the bottom 22 of the countersink. The guidance hole and/or marker hole is produced with the aid of the first portion 5' and its first cutting edges which, upon rotation 18 of the drill, drive down into the harder or solid bone at the inner and middle parts of the countersink 20 so that the hole 21 is formed. When the countersink 20 and the hole 21 have been obtained, the drill can be withdrawn in the direction of arrow 23. The direction of introduction of the drill is indicated by 24 in FIG. 4.

When the soft tissue 15 has been penetrated and the countersink 20 and the hole 21 are made, hole formation can continue using another drill (not shown in the figure) which can have a dimension corresponding to the bottom surface of the countersink. The countersink thus shaped like a truncated cone can be used for an implant (not shown) which, with its outer parts or its head, is applied in the countersink and, with its other parts, extends down into the jaw bone in the hole formed with said drill (not shown). It has been stated above that the countersink 20 has a surface shaped as a truncated cone. The countersink surface can of course have another shape, for example consisting of a cylindrical surface.

Although the foregoing systems and methods have been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. While certain embodiments of the inventions have been described, these embodiments have been presented by way of example only, and are not intended to limit the scope of the inventions. Indeed, the invention is not limited to the embodiment shown above by way of example, and instead it can be modified within the scope of the attached patent claims and the inventive concept.

What is claimed is:

1. A method of forming a hole in a jaw bone at a drill site, the method comprising:

forming an initial hole in soft tissue of the jaw bone using a first portion of a drill, the first portion disposed at a distal end of the drill, the first portion having a first width for defining a diameter of the initial hole;

advancing the first portion of the drill through the soft tissue and into a bone portion of the jaw bone to form a guidance hole in the bone portion of the jaw bone, the guidance hole having a diameter generally defined by the first width of the first portion of the drill;

advancing the drill until a second portion of the drill contacts the soft tissue to form an enlarged hole in the soft tissue, the second portion disposed at least partially intermediate the first portion and a proximal end of the drill, the second portion having a second width that is greater than the first width, the enlarged hole having a diameter that is generally defined by the second width of the second portion of the drill and is larger than the diameter of the initial hole; and further advancing the drill until the second portion of the drill contacts the bone portion of the jaw bone to form a countersink hole in the bone portion, the countersink hole having a flat bottom and an inclined surface, wherein the flat bottom is immediately adjacent to the inclined surface.

2. The method of claim 1, wherein the second portion of the drill comprises second cutting edges that are inclined with respect to a centerline of the drill, the countersink hole being produced using the second cutting edges of the second portion of the drill.

3. The method of claim 2, wherein the countersink hole is formed to define a truncated conical shape.

4. The method of claim 2, wherein the second cutting edges are inclined at an angle of about 45° in relation to the centerline of the drill.

5. The method of claim 1, wherein the first width is about 1.5 mm and the second width is about 4.7 mm.

6. The method of claim 1, wherein the first portion of the drill comprises first cutting edges that are inclined with respect to a centerline of the drill such that the guidance hole defines a generally conical bottom surface.

7. The method of claim 1, wherein the guidance hole is formed in the bone portion of the jaw bone for facilitating placement of a dental implant applied in the countersink hole.

8. The method of claim 1, further comprising using a second drill to adjust the diameter of at least one of the countersink hole and the guidance hole.

9. The method of claim 1, wherein the guidance hole is formed in a first stage and the countersink hole is formed in a second stage and the drill is withdrawn after the second stage.

10. The method of claim 1, wherein the soft tissue of the jaw bone is not cut at the drill site prior to penetration of the drill.

11. A method of forming a countersink hole and a guidance hole at a drill site of a jaw bone, the method comprising:
without previously cutting open soft tissue of the jaw bone at the drill site, advancing a drill into the drill site to form an initial hole in the soft tissue using a first portion of the drill;
advancing the first portion of the drill into a bone portion of the jaw bone until a second portion of the drill contacts the soft tissue to form an enlarged hole in the soft tissue;
further advancing the drill into the bone portion until the second portion of the drill contacts the bone portion such that the first portion forms a guidance hole in the bone portion and the second portion forms a countersink hole in the bone portion, the guidance hole extending to a depth in the bone portion that is greater than a depth of the countersink hole, the countersink hole having a flat bottom and an inclined surface,
wherein the flat bottom is immediately adjacent to the inclined surface.

12. The method of claim 11, wherein the guidance hole defines a diameter that is smaller than a diameter of the countersink hole.

13. The method of claim 11, wherein the second portion of the drill comprises second cutting edges that are inclined with respect to a centerline of the drill, the countersink hole being produced using the second cutting edges of the second portion of the drill.

14. The method of claim 13, wherein the countersink hole is formed to define a truncated conical shape.

15. The method of claim 13, wherein the second cutting edges are inclined at an angle of about 45° in relation to the centerline of the drill.

16. The method of claim 11, wherein the first width is about 1.5 mm and the second width is about 4.7 mm.

17. The method of claim 11, wherein the first portion of the drill comprises first cutting edges that are inclined with respect to a centerline of the drill such that the guidance hole defines a generally conical bottom surface.

18. The method of claim 11, wherein the guidance hole is formed in the bone portion of the jaw bone for facilitating placement of a dental implant applied in the countersink hole.

19. The method of claim 11, further comprising using a second drill to adjust the diameter of at least one of the countersink hole and the guidance hole.

20. The method of claim 11, wherein the guidance hole is formed in a first stage and the countersink hole is formed in a second stage and the drill is withdrawn after the second stage.

21. The method of claim 1, wherein the first portion of the drill comprises a pair of first cutting edges, and the second portion of the drill comprises a pair of edges extending intermediate a pair of second cutting edges and the pair of first cutting edges, the pair of second cutting edges extending at an angle relative to a longitudinal center line of the drill, the pair of edges extending from the first portion in a generally perpendicular direction relative to the longitudinal center line.

22. The method of claim 1, wherein the countersink hole has a side, and wherein the inclined surface joins the flat bottom with the side of the countersink hole.

23. The method of claim 1, wherein the flat bottom of the countersink hole joins the inclined surface of the countersink hole with a side of the guidance hole.

24. The method of claim 11, wherein the first portion of the drill comprises a pair of first cutting edges, and the second portion of the drill comprises a pair of edges extending intermediate a pair of second cutting edges and the pair of first cutting edges, the pair of second cutting edges extending at an angle relative to a longitudinal center line of the drill, the pair of edges extending from the first portion in a generally perpendicular direction relative to the longitudinal center line.

25. The method of claim 11, wherein the countersink hole has a side, and wherein the inclined surface joins the flat bottom with the side of the countersink hole.

26. The method of claim 11, wherein the flat bottom of the countersink hole joins the inclined surface of the countersink hole with a side of the guidance hole.

* * * * *